(12) United States Patent
Totoriello et al.

(10) Patent No.: US 10,317,369 B2
(45) Date of Patent: Jun. 11, 2019

(54) ACOUSTIC FREQUENCY BASED SYSTEM WITH CRYSTALLINE TRANSDUCER MODULE AND MASS COMPARATOR FOR NON-INVASIVE DETECTION OF EXPLOSIVES AND CONTRABAND

(71) Applicant: GTBM, Inc., East Rutherford, NJ (US)

(72) Inventors: Vincent Totoriello, West Caldwell, NJ (US); Richard Picolli, Rutherford, NJ (US)

(73) Assignee: GTBM, Inc., East Rutherford, NJ (US)

( * ) Notice: Subject to any disclaimer, the term of this patent is extended or adjusted under 35 U.S.C. 154(b) by 161 days.

(21) Appl. No.: 15/530,906

(22) Filed: Mar. 21, 2017

(65) Prior Publication Data
US 2018/0364198 A1    Dec. 20, 2018

Related U.S. Application Data

(60) Provisional application No. 62/499,367, filed on Jan. 20, 2017.

(51) Int. Cl.
| | |
|---|---|
| *G01N 29/04* | (2006.01) |
| *G01N 29/24* | (2006.01) |
| *G01N 29/44* | (2006.01) |
| *G01N 29/12* | (2006.01) |
| *G01N 29/30* | (2006.01) |

(52) U.S. Cl.
CPC ........... *G01N 29/043* (2013.01); *G01N 29/04* (2013.01); *G01N 29/12* (2013.01); *G01N 29/245* (2013.01); *G01N 29/30* (2013.01); *G01N 29/44* (2013.01); *G01N 29/4409* (2013.01); *G01N 2291/101* (2013.01)

(58) Field of Classification Search
CPC ............... G01N 29/043; G01N 29/245; G01N 29/4409; G01N 2291/101
USPC .......................................................... 73/629
See application file for complete search history.

(56) References Cited

U.S. PATENT DOCUMENTS

| | | | |
|---|---|---|---|
| 4,864,142 A | 9/1989 | Gomberg | |
| 5,692,029 A | 11/1997 | Huseeiny | |
| 6,442,997 B1 * | 9/2002 | Megerle | G01N 1/2273 204/406 |
| 6,667,034 B2 | 12/2003 | Palsson et al. | |
| 7,151,447 B1 * | 12/2006 | Willms | G08B 13/1654 340/540 |

(Continued)

FOREIGN PATENT DOCUMENTS

WO PCT/US2013/027932 A2    9/2013

*Primary Examiner* — Natalie Huls
*Assistant Examiner* — Monica S Young
(74) *Attorney, Agent, or Firm* — Robert Gorman; Gorman Law Offices

(57) ABSTRACT

The present invention relates to a system and method for detection of contraband such as concealed explosives, drugs, smuggled goods, etc., through the use of an acoustic frequency detector having a crystalline transducer module and mass comparator. The present invention can be employed in a non-destructive manner for the mobile and stationary inspection of object such as luggage, person, containers, etc., through a combination of computer-aided electron counting and mass analysis techniques combined with a crystalline and oil enhanced transducer that, upon return of a system-generated acoustic signal, are used to screen and confirm explosive threats and/or other contraband.

17 Claims, 9 Drawing Sheets

(56) References Cited

U.S. PATENT DOCUMENTS

| | | | |
|---|---|---|---|
| 7,450,779 B2 * | 11/2008 | Ferrari | G06K 9/40 |
| | | | 382/128 |
| 7,800,527 B2 | 9/2010 | Douglass et al. | |
| 8,019,466 B2 | 9/2011 | Ewing et al. | |
| 8,731,242 B2 | 5/2014 | Vogelmann | |
| 8,756,975 B2 | 6/2014 | Wu | |
| 9,279,796 B1 | 3/2016 | Weisberg | |
| 2003/0027936 A1 * | 2/2003 | Murray | G01N 21/7703 |
| | | | 525/384 |
| 2003/0162987 A1 * | 8/2003 | Houser | C07F 7/081 |
| | | | 556/431 |
| 2004/0220753 A1 * | 11/2004 | Tabe | G01N 33/0057 |
| | | | 702/32 |
| 2005/0259889 A1 * | 11/2005 | Ferrari | G06K 9/40 |
| | | | 382/275 |
| 2007/0023621 A1 * | 2/2007 | Blick | B82Y 15/00 |
| | | | 250/251 |
| 2009/0027280 A1 * | 1/2009 | Frangioni | A61K 49/0032 |
| | | | 343/703 |
| 2009/0038932 A1 * | 2/2009 | Denslow | B01F 5/10 |
| | | | 204/157.15 |
| 2010/0320372 A1 * | 12/2010 | Blick | G01N 23/00 |
| | | | 250/282 |
| 2011/0004091 A1 * | 1/2011 | Brooks | A61B 5/0093 |
| | | | 600/407 |
| 2012/0176237 A1 * | 7/2012 | Tabe | A61B 5/6804 |
| | | | 340/539.12 |
| 2014/0150555 A1 * | 6/2014 | Ikushima | G01N 29/043 |
| | | | 73/596 |
| 2017/0205377 A1 * | 7/2017 | Garnett | G01N 21/636 |
| 2018/0074024 A1 * | 3/2018 | Schlereth | G01N 29/12 |

\* cited by examiner

ACOUSTIC FREQUENCY BASED SYSTEM WITH CRYSTALLINE TRANSDUCER MODULE AND MASS COMPARATOR FOR NON-INVASIVE DETECTION OF EXPLOSIVES AND CONTRABAND

BACKGROUND OF THE INVENTION

Acoustic frequency detection and wave based systems are known in manufacturing and oil industries for imaging and non-destructive evaluation (NDE) of materials. Such systems may involve the propagation of energy through solids, liquids, and gases as waves; typically a pulse of energy is applied to an object to be imaged and reflected waves of the pulse are detected and processed for imaging. The spatial relationship and amplitude of the reflected waves provide information as to the location and nature of structures that reflected the acoustic energy in the object being analyzed.

NDE of objects for detection of contraband and/or explosives is known according to some specific approaches. Such NDE approaches may include acoustic frequency detection or vision-based systems such as infrared, Millimeter Wave (MMW), multispectral, hyperspectral, infrared, X-ray, or imaging radar output. However, such systems have significant limitations. For example, known ultrasound based systems employ pulses, the generator of which must be physically applied to an object through surface contact, preferably through a medium such as gel or the like. Additionally, ultrasound is less effective at penetrating heavy clothing than other systems, such as radar.

Likewise, other systems, such as MMW and imaging radar systems are similarly limited in penetration of certain materials. Separately, infrared sensing systems can be impractical due to very small temperature contrasts that may exist between hidden contraband and outer layers of covering material of a given container. Although X-ray and magnetic portal detector systems have proven much more effective at detecting both metallic and non-metallic concealed weapons than some of the above systems, such "portal" detection technologies are inherently limited by the inability to operate in a mobile fashion, and at any rate, do not necessarily identify certain types of explosives and most narcotics.

In each of the above cases, known systems do not provide for mobile applications, nor do they detect disparate categories of contraband, whether narcotics, smuggled gems, illicit quantities of cash, various chemical categories of explosives, or biological agents. Accordingly, known approaches are limited in terms of protective applications and mobile field usage.

SUMMARY OF THE INVENTION

Methods and apparatus are described for acoustic wave detection of elements and elemental analytes. To this end, the present invention relates generally to methods of utilizing of acoustic energy produced from novel crystalline and oil-enhanced transducers, more particularly to methods of using such acoustic energy for mobile and stationary detection of explosives and contraband by detecting the signature of desired or "flagged" elements and the analytes thereof by use of a mass comparator. Unlike known ultrasound and other similar systems, the present invention utilizes a novel crystalline, oil-suspended piezoelectric transducers to generate acoustic pulses that transmitted into the object to be analyzed and subsequently, to detect reflected waves received at the transducer.

The present invention offers short-range detection of materials containing certain "flagged" elements, such as nitrogen and other elements that may indicate explosives or other contraband. Unlike other technologies, the present detection system can discriminate among different types of contraband. for example, where an element such as Nitrogen (in the case of explosives detection field of use) has been pre-programmed in the given field of use as a "flagged" element, the system can accurately identify explosives and distinguish them from benign Nitrogen compounds, because the response from each Nitrogen compound that it detects has a unique spectral analysis signature.

More specifically, the invention contemplates, in achieving the above, the use of a wand or other similarly portable means of identifying the presence of various types of explosives in a non-invasive fashion through use of specialized data calculator hardware and software configured for receiving and comparing the mass spectrometry signature ratio with known elemental flags, such as Nitrogen, Phosphorus, etc. However, the inventive system offers features which also make it viable for use in detection of non-explosive materials, such as biological aspects, narcotics, illegal contraband such as smuggled gems or currency, etc., based upon the respective elemental signatures that each of the above normally exhibit.

One method of the present invention therefore includes a oil-based crystalline suspension transducer, operatively positioned as part of a head or wand terminus of an acoustic detector, for the purpose of transmitting an output signal. Once the output signal has been reflected by the existing target object materials (including, specifically, the "flagged" elements, if present) is received back at the detector head and then either detected with a charge-coupled-device (CCD) array with the information being electrically communicated to the signal processing assembly or sent directly to a mass calculator.

In affording the above, the present invention therefore provides for the following beneficial advances relating to: (1) Provision of a molecular detection hardware module for non-invasive mass analysis of derived molecular (mass spectrometry) signatures that are compared, utilizing a novel molecular signature software, against calculated molecular or mass signature ratio standards and/or a resonant frequency signature; (2) Provision of the entire system (or, in other embodiments, substantially the entire system) in a portable, dust-proof and shock proof contained wand-based system; (3) Provision of the molecular detection module having novel sensor surfaces, either chemical vapor deposition process metallicized surfaces, or novel oil-suspension ceramic crystals; (4) by providing an optional sealed oil suspension tip to propagate acoustic waves without the need for physical contact with a given subject item; and (5) Provision of a stationary or mobile system with optional detachable wand. By contrast, no known system affords these advantages, and accordingly, the present invention overcomes the aforementioned and other disadvantages inherent in the prior art.

DETAILED DESCRIPTION OF THE INVENTION

In terms of potential fields of application, the present invention relates to inspection systems such as those used to inspect luggage, packages or other target objects to determine the presence of contraband such as explosives, weapons or drugs. A more specific example is the inspection of luggage that is to be checked onto airline flights or carried on to an airplane. In one aspect the invention relates to the use of acoustic waves for the detection of explosives or other contraband, such as may be concealed in said target objects.

Figure 1:
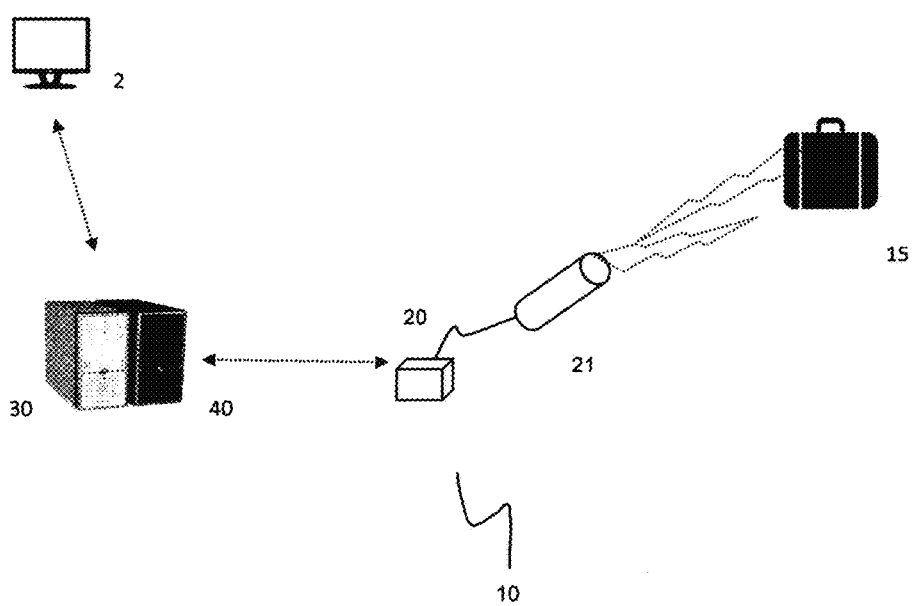
FIG. 1 is a block diagram of an acoustic frequency detection system comprising the present invention being used in an illustrative operating environment on a target object.

FIG. 1 illustrates an acoustic wave system 10 for analyzing an examination object or target 15 with acoustic energy comprising an acoustic frequency module 20, alternatively referred to herein as acoustic frequency detector 20, a signal processing assembly 30, and a display and analysis module 40. Acoustic frequency detector 20 is acoustically coupled to or directed at target object 15 such that acoustic energy is both transmitted from, and when reflected from target object 15, received by acoustic frequency detector 20. In one example of the present invention, acoustic frequency detector 20 may be adapted so that when reflected from target object 15, acoustic energy incident on the transmit/receive surface of wand 21 registers a modulation in an electronic array. This modulation is converted to a readout signal emanating from acoustic frequency detector 20 (wand 21), which is in turn is operatively connected to signal processing assembly 30, such that a processed output signal corresponding to the received acoustic energy is generated for conversion by signal processing assembly 30. Display 2 and analysis module 40 is operatively connected to processing assembly 30 so that the processed output signal is visually presented or otherwise analyzed. Unlike various acoustic based systems such as ultrasound, the present invention is acoustic wave based and includes the novel crystalline oil suspension based wand 21 that need not be physically touching target object 15. The intention is to generate a signal having a frequency narrow enough to reach the object within, in one embodiment, a certain fine tuned range from that object. In some cases this acoustic energy may spread out upon penetration of the materials making up target object 15, and will be reflected back to transmit/receive surface wand 21.

Wand 21 of acoustic frequency detector 20 therefore need not touch the object but can be just swiped near objects such as luggage. The proper wavelength and frequency of the wave to encompass the entire given target object may vary depending on what restricted material is being sought (e.g. cash, narcotics, gems, precious metals, or type of explosive) and its chemical composition or "signature". Additional factors or settings such as power, amplitude, materials, and the like typically do not alter the aforementioned processes once transducer 25 of the inventive system has been fine tuned in a given field application as described herein because the inventive approach is to employ an initial wave for penetration of target object 15, and based upon the response thereto, as second wave may be generated at a maximized distance therefrom so as to transmit the second wave to penetrate within target object 15 and bounce or reflect from whatever contraband material(s) may be detected therein. Accordingly, the fine tuning may be accomplished by employing a device such as an oscilloscope to determine the maximum the practical distance of use away from the surface(s) of target object 15 to be scanned in the field of use, as well as by the size and/or particular type of material(s) that target object 15 is comprised of, in addition to the aforementioned signature setting. In one embodiment, such fine tuning and adjustments can be made with the assistance of an oscilloscope that will indicate when the wave parameters and/or distance of usage is such that accuracy is being compromised by lack of usable data. For example, the illustrative oscilloscope will indicate frequency and wavelength upon setting the oscilloscope to detect the resonant frequency of Nitrogen (whether liquid and/or solid. The range of the oscilloscope can be adjusted to just look for target frequency ranges. In this illustrative case, the resonant frequency of the atom Nitrogen has a Frequency of 28.905 MHz (something which is understood by those skilled in the art to be well documented by nuclear magnetic resonance sampling), and as such, a user setting the initial fine tuning can set the oscilloscope to detect the wave forms that are detected only in the frequency range of say, 20 to 30 MHz. With this approach in mind, the user doing the initial fine tuning can then start detecting the presence of such wave forms, and if the detector finds a match, the oscilloscope will reveal this by matching the frequency and waveform that is returning, and in order to make sure the waveform and frequency are a match, the user that executes the initial fine tuning can also adjust the detector itself, using the oscilloscope to lock down the optimal distance of the inventive acoustic wave system 10 from target object 15. Having said this, where acoustic wave system 10 is initially situated from target object 15 by taking a sample reading which determine by experimentation how close the user needs to place acoustic wave system 10 from target object 15. Consequently, once the user has fine tuned the settings and distance, illustrative boundaries from target object 15 may be termed the "range of detection" or "range of use" for one given field of application. However, one skilled in the art can nevertheless appreciate that these parameters can vary depending on field of use, such that the "range of detection" or "range of use" for other given fields of application may very well differ accordingly. Considering this dynamic, the aforementioned parameters can therefore be easily adjusted to match the proper range of detection. In one alternative embodiment involving exemplary usage of detection of explosives in airline luggage as further described hereafter, the effective maximum range for useful readouts for detections of Nitrogen (N) based signatures, or as otherwise may be determined.

Figure 2A:
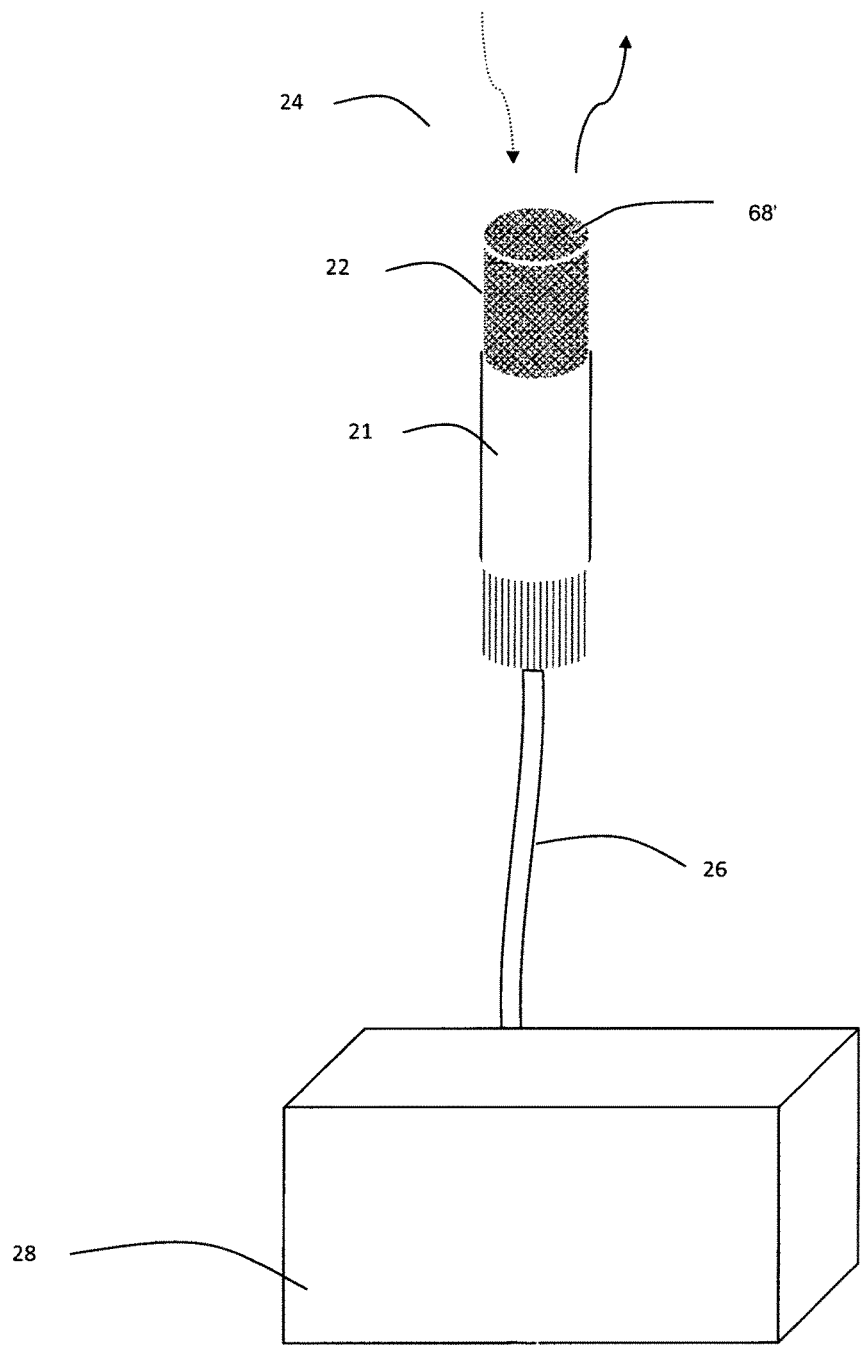
FIGS. 2 A-2B are exemplary diagrams of a wand of the present inventive system, illustrating one embodiment of the novel crystalline oil suspension tip wand terminus and connected counter, calculator and interface(s)

With reference to FIG. 2A a simple configuration of an acoustic frequency detector 20 made up of a fixed transmitter/detector array (transmit/receive surface) 68' at tip 22 of wand 21, coupled via connection 26 with an electron counter 28 via transducer 25 (as seen hereafter in FIG. 2B) that is emitting acoustic waves at 24 (output signal) which will thereafter be reflected back at 24 to array 68' of acoustic frequency detector 20. Once so provisioned, incoming wave 24 will offer the inventive system 10 all the information needed for properly scanning and outputting an analysis of the presence (or absence) of any flagged materials within target object 15. Essentially, and as further shown in FIG. 2B, signal returns to acoustic frequency detector 20 are passed on to electron counter 27 via transducer 25 to data calculator (standard) 29 in order to convert the signal(s) from an acoustic wave, to an electromagnetic wave as output at 29'. This output represents the information required to detect the parameters of the atomic structure of material(s) in target object 15. However, the aforementioned electromagnetic wave is, in one embodiment, first input through electron counter 27 (in FIG. 5 hereafter, referred to as 50), so that electrons can be accounted for from each molecule and subsequently, continue on to data calculator 29, and then through an associated processor chip (not depicted). Detectors may be located on the same side of the item as transmitters (transducer) or in any other suitable location. In some embodiments, transmitters should preferably not be active while detectors are measuring reflected sound waves to avoid interference. More complicated detector and transmitter array configurations may be employed. For example, a transmitter array may be positioned on one side of the item and a detector array may be positioned on another side of an item. Such a configuration may be used to detect acoustic waves reflected from the target. In another example, both transmitted and reflected waves may be detected. To avoid interference, it may be preferable to position a detector measuring reflected waves for a reflection measurement orthogonal (at a right angle) to a transmitter providing waves for a transmission measurement.

In one embodiment of the invention data calculator 29' can be used to calculate mass. Alternatively, in another embodiment, transducer 25 seen in FIG. 2B can replace data calculator 29' for reasons described below. Specifically, in such an alternative embodiment, data calculator 29' may be obviated through the use of transducer 25 for mass value determinations as follows. At the onset, it is understood that the mass of an isotope is equal to the number of protons plus the number of neutrons in the nucleus but that the mass of an ion, being essentially close to zero by comparison may be ignored when finding the mass number. With the understanding that the mass number of an ion is the same as that of a neutral atom, it is functionally noted that transducer 25 generates pulses from an echo sounder which in turn has received high voltage electrical pulses, and thereafter, the returning sound wave coming passes through transducer 25 mass and is carried along with the neutral atom, which is then converted into an ion passing through electron counter 27. The echo sounder (not depicted) within transducer 25 can calculate the time difference between a transmit pulse and the return echo and can be easily understood by the user or computer. More specifically, for the echo sounder in computations within the context of say, linear media, any wave pattern can be described in terms of the independent propagation of sinusoidal components. The wavelength $\lambda$ of a sinusoidal waveform (wavelength) traveling at constant speed $v$ is given by $\lambda=c/f$ where $v$ is the phase speed (magnitude of the phase velocity) of the wave and $f$ is the wave frequency. In a dispersive medium, the phase speed itself depends upon the frequency of the wave, making the relationship between wavelength and frequency nonlinear. In the case of electromagnetic radiation, the phase speed is close or approximately the speed of light, about $3\times10^8$ m/s. Thus, the wavelength of say, a sound wave that is 30 Hz, is determined to be 5 meters when calculated in accordance with the above equation that relates wavelength as being equal to the speed of wave (e.g., approximately that of light), divided by the frequency. Once this is determined, the echo sounder can back calculate to get both frequency and wavelength through use of $E=h\nu$ where E=energy, h=Planck's constant=$6.626\times10^{-34}$ J·s and $\nu$=frequency. The echo sounder may employ a second equation, the wave equation, which describes the speed of light in terms of wavelength and frequency: $c=\lambda\nu$; where c=speed of light=$3\times10^8$ m/sec, $\lambda$=wavelength, and $\nu$=frequency, but rearranges the equation to solve for frequency: $\nu=c/\lambda$. Next, the echo sounder replaces frequency in the first equation with $c/\lambda$ to get a formula by using: $E=h\nu$; and $E=hc/\lambda$, and by plugging in the following values to derive the mass: $E=6.626\times10^{-34}$ J·s$\times3\times10^8$ m/sec/(633 nm$\times10^{-9}$ m/1 nm); and $E=1.988\times10^{-25}$ J·m/$6.33\times10^{-7}$ m $E=3.14\times10^{-19}$ J.

Figure 3:
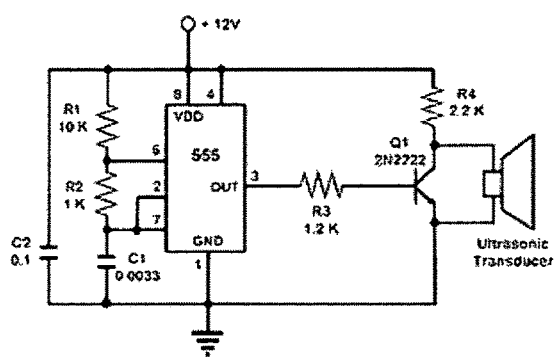
FIG. 3 is an electronic schematic diagram of an acoustic frequency propagator and detector illustrating another embodiment of the present invention.

FIG. 3 illustrates one possible variant of an electronic schematic diagram of acoustic frequency propagator and detector 20, essentially an acoustic wave generator and receiver. The acoustic waves generated therefrom may take various forms, whether acoustic surface, guided, shear, compressive, or bulk waves. At least one acoustic wave is first propagated through the material of the target, and a reflection or return of the acoustic wave is detected, and an acoustic wave parameter is determined therefrom. This parameter is then converted by a value signal processing assembly 30 into a signature that illustratively, after mass analysis, may be compared against a look up table (standard, as further delineated illustratively hereafter in FIG. 4) of signatures of various elements and their analytes, or calculated molecular or mass signature ratio standards. As will be discussed hereafter in regards to FIG. 8, any false positive analysis will be conducted once this signature determines the presence of a given "flagged" element (if present). To this end, further computations can be run by a special purpose processor circuit (not depicted) having instructions configured to differentiate between false positives as detailed in FIG. 8.

Figure 4:
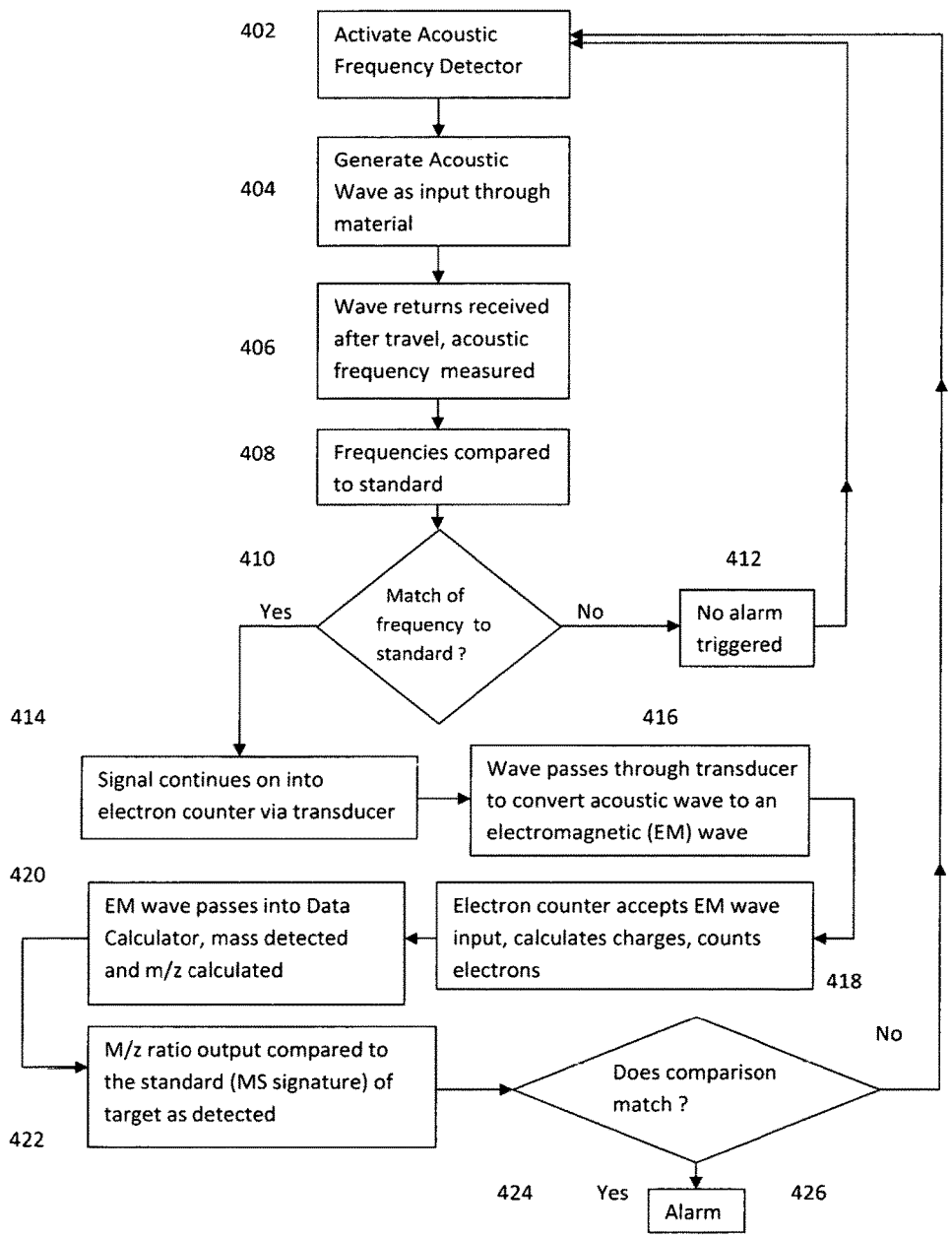
FIG. 4 is a flow diagram indicating illustrative instructions for the special purpose circuit configured to differentiate between false positives amongst signatures of "flagged" elements, illustrating yet a further embodiment of the present invention.

FIG. 4 details an illustrative flow process rendering instructions for the special purpose circuit 29" configured to differentiate between false positives amongst signatures of "flagged" elements. As detailed therein, acoustic frequency detector 20 is activated at step 402, which generates an acoustic wave at 404 for propagation to and within material(s) of target object 15, the process of which ultimately yields a reflected wave which returns to surface 68' of acoustic frequency detector 20 for frequency measurement at step 406. Any frequency or frequencies are then compared to a standard, which in one illustrative embodiment would be the ratio output of say, Nitrogen, which has a well known ratio that returns a specific frequency at step 410, and if a given frequency does not match the respective flagged material(s) frequency, then no alarm is triggered at step 412, and a return to the beginning of the process at step 402 is directed, thereby effectuating the first of two parts of the innovative "bifurcated double verification" that eliminates false positives during flagging of suspicious materials. by contrast, however, if the given frequency does match the respective flagged material(s) frequency, then an alarm may or may not yet be triggered as the signal continues, via transducer 25, to electron counter 27 at step 414, but first is converted by transducer 25 from an acoustic wave signal into an electromagnetic (EM) wave at step 416. Once converted, electron counter 27 receives the EM wave signal as input at step 418, and calculates charges and counts electrons. Electron counter 27 needs to calculates charges and counts electrons because, by being an EM wave returning at transducer 25, it will now convert everything to an ion in order that the electrons and charge can be accordingly determined. In addition, the diodes in electron counter 27 only allow flow one way, that is, back to the data calculator so there is no interference from another stream flowing back the other way. This feature also functions to protect electron counter 27, as well as to allow it to make its calculation without any noise or interference. Thereafter, the EM wave signal passes into data calculator 29, which detects the mass and calculates the m/z ratio at step 420, as described hereinafter. Once the m/z ratio is output by data calculator 29, it is compared to a standard such as the mass spectrometry signature of Nitrogen is both well known and unique. The mass spectrometry signature of Nitrogen exhibits what is termed peaks of relative abundance at 13 MHz and 28 MHz, and it is these peaks that may be employed as its signature because no other element exhibits these two same peaks. As such, this signature offers a useful way of analyzing the returning input wave, and also, offers the feature of an output that can be transmitted to a special purpose computer chip that acts akin to a "Traffic Cop" that directs the flow of signal data for processing, such that "permitted flows" are those that are detected signals that are compared to this signature, and permitted further processing based upon the resulting match of with the signature It is noted however, that this standard is different from the standard described at step 410 in that the first standard referenced heretofore is the resonant frequency of the element Nitrogen, detected at 28.905 MHz, such that the wave will continue on then pass through the electron counter and data calculator, but thereafter, the second standard comes into factor, as it is stored as the mass spectrometry signature of Nitrogen. If both standards produce positive matches or otherwise pass the test when compared to each other, then the following will happen if there is a comparison match between the m/z output at step 424, then an alarm is sounded at step 426, thereby effectuating the second part of the innovative "bifurcated double verification" that eliminates false positives during flagging of suspicious materials. It is noted that as used herein, the baseline value for contraband materials can therefore be either the "first" standard ("signature") referenced above, the "second" standard ("signature") referenced above, or both in combination.

Figure 5:
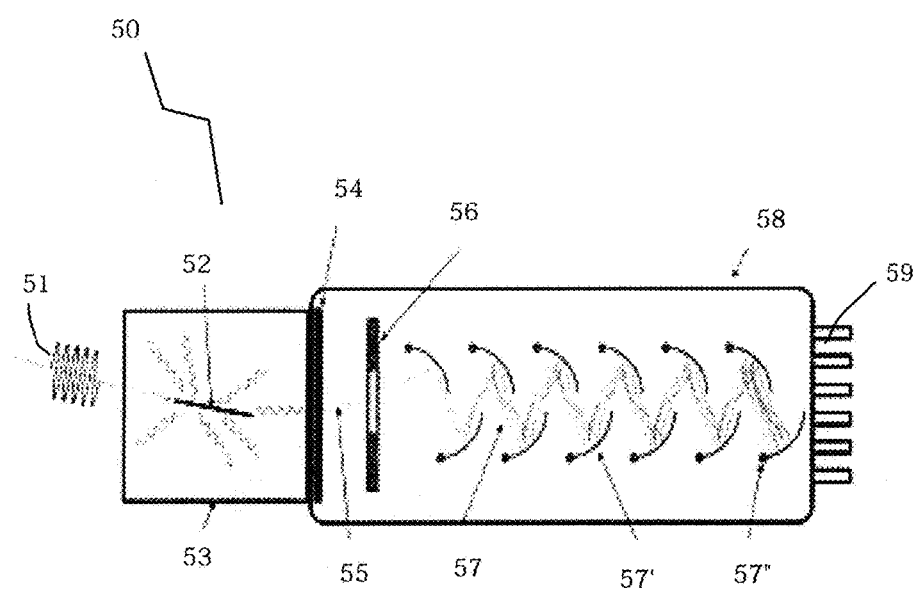
FIG. 5 is an electronic schematic diagram of an electron multiplier in one embodiment of the present invention.

As referenced above, the electron counting process is effectuated through use of electron counter 27 (alternatively termed a photomultiplier), is used as the first part of the "bifurcated double verification" of the previously derived signature, thereby preventing the generation of false positives. In order to do so, electron counter 27 should feed output in terms of resulting values, such as milli-Volt (mV) labeled numerical indicia to mass calculator 70 (alternatively termed mass analyzer, seen in FIG. 7), or vice versa, where mass calculator 70 is fed results coming out of electron multiplier 50 as seen in FIG. 5. As one skilled in the art might appreciate, the exact configuration may vary because the relative advantage of the feed process is an accurate and quick readout, while the disadvantage of this approach is the potential for resulting electrical problems in the unit.

Accordingly, FIG. 5 details electron counter 50, which has the purpose of converting returning wave to a EM via transducer 25 and then using diodes which will only permit flow in one direction, thereby eliminating noise and any interference from a wave coming from the other direction. This feature protects electron counter 27 and additionally, the diodes use light (photons) to attract the ions into it as well as protect the diodes from lack of use given that the photons also will constantly be recharging the diodes. The photons thereof are therefore generated inside electron counter 27 typically for the aforementioned reasons. As seen therein, high energy photons 51 enter scintillator 53 which uses an ionization track 52 to alter the same to low energy photons. Connected thereto is a photomultiplier tube 58, with connector pins 59 at one end, a photocathode 54 emitting primary electron at 55 for concentration through focusing electrode 56 such that secondary electrons 57 are generated across dynode 57' and anode 57".

Figure 6:
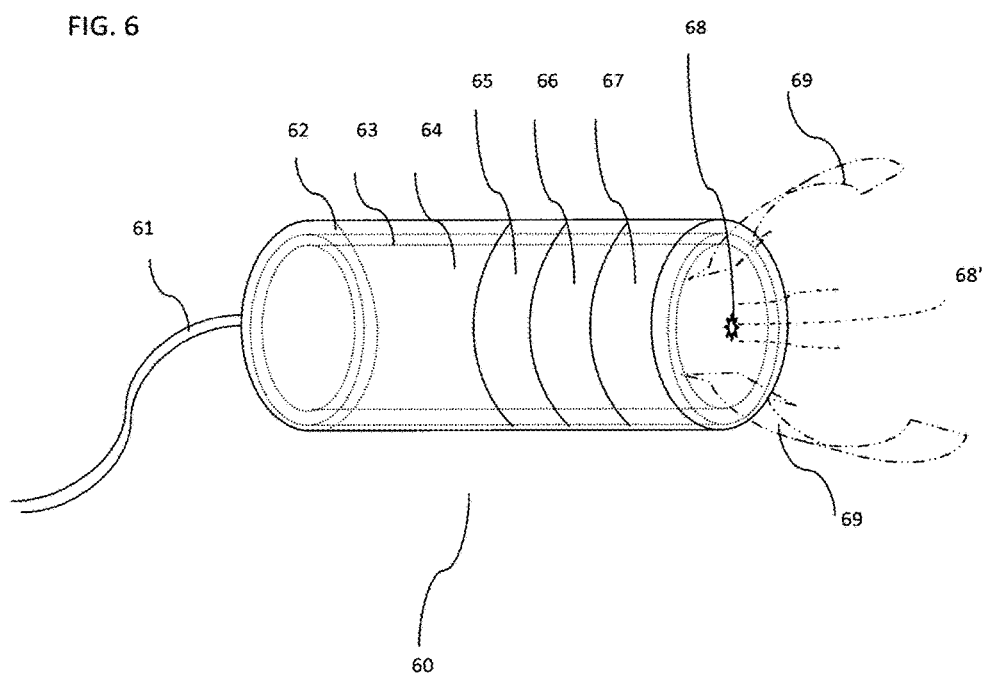
FIG. 6 is an electronic schematic diagram of an acoustic frequency propagator and detector illustrating another embodiment of the present invention.

FIG. 6 details a yet more advanced and innovative variant 60 of transducer 25, connected via connector 61 to acoustic wave system 10. Therein, one embodiment entails provision of an encased electrical shield 62, acoustic insulator 63, damping element 64, and illustratively, PZT, or lead zirconate titanate $(Pb[Zr(x)Ti(1-x)]O_3)$, is a piezoelectric ceramic material that, when fired, has a perovskite crystal structure, each unit of which consists of a small tetravalent metal ion in a lattice of large divalent metal ions. In the case of PZT, the small tetravalent metal ion is usually titanium or zirconium. The large divalent metal ion is usually lead. Under conditions that confer a tetragonal or rhombohedral symmetry on the PZT crystals, each crystal has a dipole moment. PZT materials, and piezoelectric materials more generally, exhibit a unique range of properties. In a basic sense, if a piezoelectric material is deformed, an electric charge is generated in what is known as the piezoelectric effect. The opposite of this phenomenon also holds true: If an electric field is applied to a piezoelectric material, deformation occurs in what is known as the inverse piezoelectric effect. In comparison to other metallic oxide based piezoelectric material Barium Titanate ($BaTiO3$), PZT materials exhibit greater sensitivity and can handle higher operating temperatures. To this end, in one embodiment of acoustic wave system 10, PZT materials are employed so that when active, will not overheat or be affected by temperature. As such, provided therewith are PZT (active element) 65, 66, matching layer 67 forming array 68 for propagation 68' of electrical energy into waves and reception of acoustic waves 69. Typically, matching layer 67 will be structured to form ¼λ, of the wavelength of a return in one embodiment. Similarly, PZT 65, 66 will be structured to form ½λ of the return wave, which is then modified as it passes through transducer 25, in order to fine tune the output and so as to penetrate what is being examined or detected in target object 15.

Figure 7:
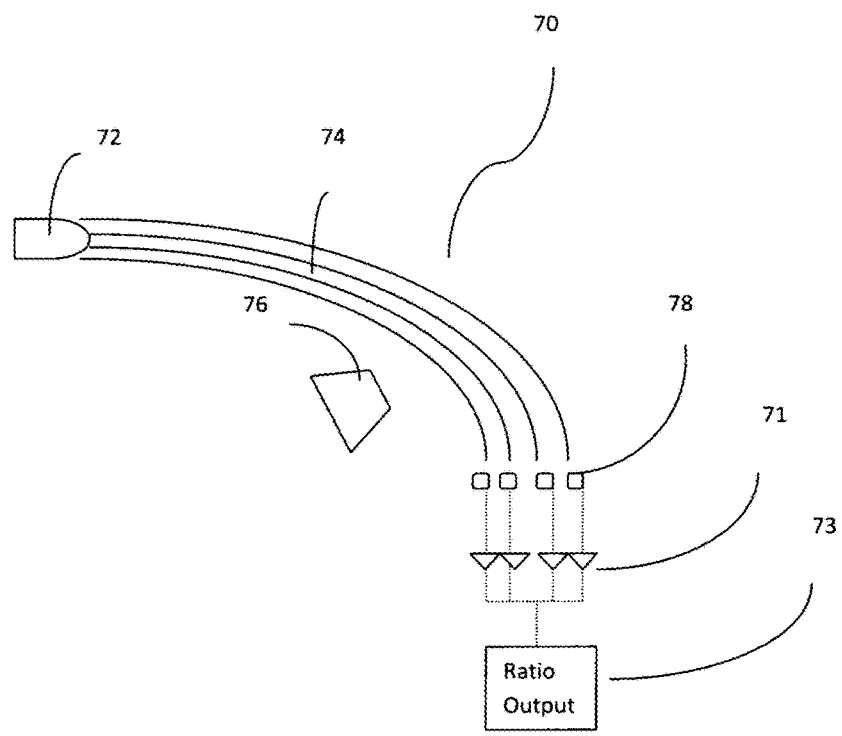
FIG. 7 is an electronic schematic diagram of a mass analyzer in one embodiment of the present invention.

FIG. 7 details an aspect of operation of data calculator 70. As illustratively depicted in FIG. 7, data calculator 70 is used to calculate mass spectrometry signature as what is termed the "m/Q ratio", as will be described in greater detail hereafter. In one embodiment, data calculator 70 may include ion source 72 for forming positive ion beam 74 which is manipulated through use of magnet 76 in order to differentiate various mass identities therein which may be collected by Faraday collectors 78 for gates of current that can respectively be generated for output through amplifiers 71, all of which is output at 73 as a ratio output. Once the EM enters data calculator 27, the charge and amount of electrons will already be detected because the acoustic wave return has been converted to an EM wave at this point and has been ionized. As used, data calculator 27 will employ electric and magnetic fields to apply a force on charged particles (ions). The relationship between force, mass, and the applied fields can be summarized in Newton's second law and the Lorentz force law: F=ma (Newton's second law) F=e (E+v×B) (Lorentz force law) where F is the force applied to the ion, m is the mass of the ion, a is the acceleration, e is the ionic charge, E is the electric field, v×B is the vector cross product of the ion velocity and the applied magnetic field from Newton's second law. It is apparent that the force causes an acceleration that is mass dependent (this is how the inventive component traps the mass, and it is for this reason that the inventive approach is mass dependent in one embodiment), and further, the Lorentz force law tells us that the applied force is also dependent on the ionic charge. Therefore, it should be understood that mass spectrometers separate ions according to their mass-to-charge ratio (m/z), rather than by their mass alone, and given that the charge z can be determined, mass can also be calculated once the charge the charge has been calculated by a special purpose chip which uses a known relative abundance and the determined charge to calculate the given mass.

Figure 8:
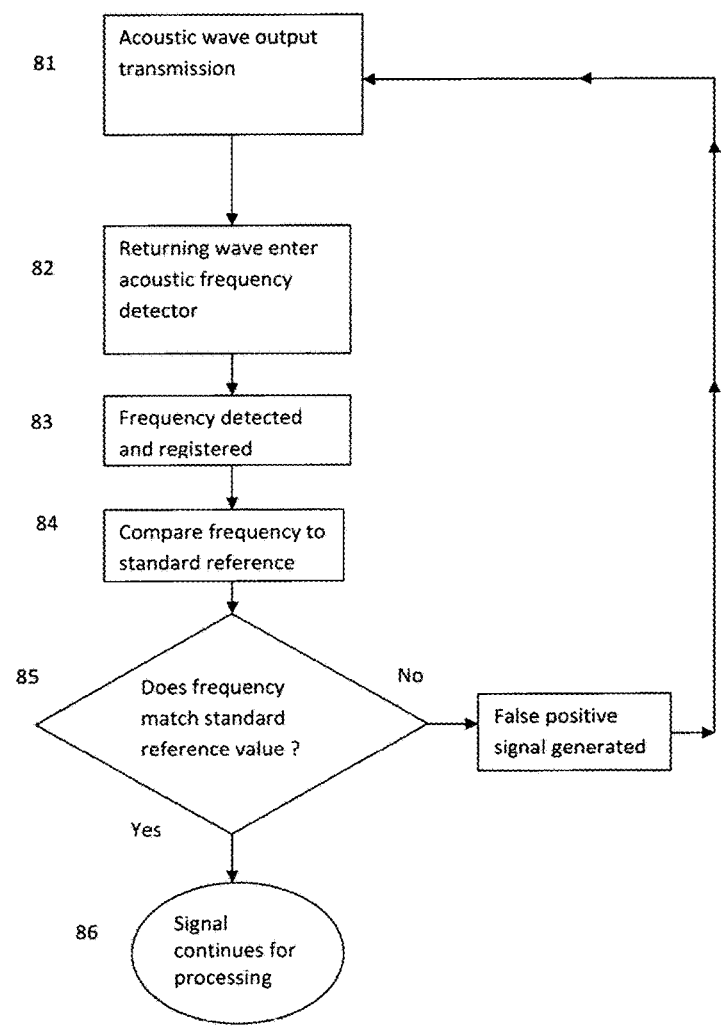
FIG. 8 is a flow diagram indicating further details of some illustrative instructions for the special purpose circuit that is configured to differentiate between false positives of the present invention.

With the above operation in mind, and with ongoing reference to FIGS. 1, 2A-2B, 4, and 7, a "flagged" element such as Nitrogen might be detected through use of a penetrating beam of acoustic frequency after passing through, and being reflected from, target 15 (e.g., baggage or person as seen in FIG. 1), where the processing steps of determining the signature of the flagged Nitrogen, when compared to a standard, generates an alarm that Nitrogen has been detected, as further detailed hereafter in FIG. 4. This will be achieved by sending the signal from acoustic frequency detector 20 to electron counter 27, which will count electrons and pass this off to data calculator 29 which will determine the elements being detected. An interface will utilize specialized software to convert or transform this signal (via a special purpose processor) in order to compare it to the selected standard, so when (if) nitrogen is detected an alarm will be triggered. As can be seen in FIG. 8, a second part of the "bifurcated double verification" that eliminates false positives during flagging of suspicious materials begins with the acoustic wave transmission at step 81, whereupon the returning wave reaches transducer 25 at 82, and the frequency is detected then registered at 83, with subsequent comparison to a standard reference at 84 via said specialized software. Thereafter, a determination is made as to whether the frequency matches the standard reference value at step 85, such that if the comparison does not match, a false positive signal (no alarm) is indicated, for ultimate restarting of the overall process, and where the comparison does, the signal continues along the process for alarm resolution.

Accordingly, the motion of any given acoustic wave will be affected by the medium through which it travels. Thus, changes in one or more of four easily measurable parameters associated with the passage of a high frequency sound wave through a material transit time, attenuation, scattering, and frequency content can often be correlated with changes in physical properties such as hardness, elastic modulus, density, homogeneity, or grain structure. As such, acoustic frequency detection according to the present invention may utilize the range of frequencies from approximately 20 KHz to 100 MHz, with most work being performed between 500 KHz and 20 MHz, but in the illustrative case of Nitrogen, will range from 20 MHz-40 MHz, all of which can be easily adjusted depending on the particular element being flagged as further discussed herein. Both longitudinal and shear (transverse) modes of vibration are commonly employed, as well as surface (Rayleigh) waves and plate (Lamb) waves in some specialized cases. Because shorter wavelengths are more responsive to changes in the medium through which they pass, many material analysis applications will benefit from using the highest frequency that the test piece will support. Sound pulses are normally generated and received after reflection, by piezoelectric transducers that have been acoustically coupled or are otherwise in proximity to target object 15. In most cases a single transducer 25 coupled or directed at one side of target object 15 serves as both transmitter and receiver (pulse/echo mode), although in some situations involving highly attenuating or scattering materials, separate transmitting and receiving transducers on opposite sides of the part may be used (through transmission mode). A sound wave is launched by exciting transducer 25 with a voltage spike or square wave. The sound wave travels through the test material, either reflecting off the far side to return to its point of origin (pulse/echo), or being received by another transducer at that point (through transmission). The received signal is then amplified and analyzed. A variety of commercial instrumentation is available for this purpose, utilizing both analog and digital signal processing.

A significant advantage of this novel acoustic frequency detection scanning over other material analysis methods is that it can often be performed in-process or on-line. High frequency sound waves can often be successfully transmitted into and out of moving materials without direct contact, through the use of a water bath, oil phase or water stream as a coupling medium. Measurements can also be performed within closed containers by coupling sound energy through the wall. Because sound waves penetrate through the test specimen, material properties are measured in bulk rather than just on the surface. It is sometimes even possible, through the use of selective gating, to analyze just one layer of a multi-layer, multi-material fabrication. The relevant measurement parameters will typically be one or more of the following:

(a) Sound velocity/pulse transit time: Sound velocity is usually the easiest acoustic frequency detection parameter to measure. The speed of sound in a homogenous medium is directly related to both elastic modulus and density; thus changes in either elasticity or density will affect pulse transit time through a sample of a given thickness. Additionally, varying degrees of non-homogeneity may have an effect on sound velocity.

(b) Attenuation: Sound energy is absorbed or attenuated at different rates in different materials, governed in a complex fashion by interactive effects of density, hardness, viscosity, and molecular structure. Attenuation normally increases with frequency in a given material.

(c) Scattering: Sound waves reflect from boundaries between dissimilar materials. Changes in grain structure, fiber orientation, porosity, particle concentration, and other micro-structural variations can affect the amplitude, direction, and frequency content of scattered signals. Scatter effects can also be monitored indirectly by looking at changes in the amplitude of a back wall echo or a through-transmission signal.

(d) Frequency (spectral) content: All materials tend to act to some degree as a low pass filter, attenuating or scattering the higher frequency components of a broadband sound wave more than the lower frequency components. Thus, analysis of changes in the remaining frequency content of a selected broadband pulse that has passed through the test material can track the combined effects of attenuation and scattering as described above.

In some applications, acoustic frequency detection data such as velocity can be directly used to calculate properties such as elastic modulus. In other cases, Acoustic frequency detection testing is a comparative technique, where in order to establish a test protocol in a given application it will be necessary to experimentally evaluate reference standards representing the range of material conditions being quantified. From such standards it will be possible to record how sound transmission parameters vary with changes in specific material properties, and then from this baseline information it will be possible to identify or predict similar changes in test samples.

A wide variety of acoustic frequency detection variants can be used in the inventive material analysis applications. Sound velocity can be measured with simple hand-held acoustic frequency detection thickness gages, while velocity, attenuation, and scattering effects can all be observed with modern digital flaw detectors. Pulsar/receivers with appropriate auxiliary equipment and acoustic frequency detection imaging systems with appropriate software can be used to quantify all of these properties, and to perform spectrum analysis (frequency content) testing as well also on both instrumentation and transducer recommendations for specific tests can be achieved.

The following is a summary of some specific, presently known material analysis applications where acoustic frequency detection techniques may be employed within the context of the present invention:

Elastic modulus: Young's modulus and shear modulus in homogenous, non-dispersive materials can be calculated from longitudinal wave and shear wave velocity (along with material density). Use of specialized waveguides can permit measurement at high temperatures.

Nodularity in cast iron: Both the concentration of graphite in cast iron and its shape and form can be quantified through velocity measurements.

Cure rate in epoxies and concrete: The speed of sound in these materials changes as they harden, thus sound velocity measurements can be correlated to the degree of curing. Concrete testing usually requires access to both sides for through-transmission coupling.

Liquid concentrations: The mixture ratio of two liquids with dissimilar sound velocities can be correlated to the sound velocity of the solution at a given temperature.

Density of slurries: The liquid/solid mix ratio of slurries such as drilling mud and paper slurry at a given temperature can be correlated to sound velocity and/or attenuation.

Density in ceramics: Uniformity of density in both green and fired ceramics can be verified by means of sound velocity measurements.

Food products: A wide variety of tests have been reported, including age of eggs and potatoes, ripeness of fruits, fat content in beef, and percent of solids in milk. Generally these tests are both nondestructive and non-contaminating.

Polymerization in plastics: In plastics and other polymers, variations in molecular structure such as length or orientation of polymer chains will often result in corresponding changes in sound velocity and/or attenuation.

Particle or porosity size and distribution: Changes in the size or distribution of particles or porosity in a solid or liquid medium will affect the amplitude and frequency of scattered acoustic frequency detection.

Grain size in metals: Changes in grain size or orientation in steel, cast iron, titanium, and other metals will cause changes in the amplitude, direction, and/or frequency content of scattered acoustic frequency detection.

Anisotropy in solids: Variations in sound velocity, scattering, and/or attenuation across different axes of a solid can be used to identify and quantify anisotropy, including molecular structure and electron scattering.

Case hardening depth in steel: High frequency shear wave backscatter techniques can be used to measure the depth of case hardening.

Illustrative of examples of acoustic detection devices that may be employed within the context of the present invention are as follows: (i) An acoustic frequency detection device, utilizing high frequency sound waves reflect from flaws in predictable ways, producing distinctive echo patterns that can be displayed and recorded by portable or stationary instruments, where sound waves, expressed as organized mechanical vibrations traveling through a solid, a liquid, or a gas medium such as those that might be found in target object 15. These waves will travel through a given medium at a specific speed or velocity, in a predictable direction, and when they encounter a boundary with a different medium they will be reflected or transmitted according to simple rule, but are completely nondestructive and safe; (ii) An acoustic frequency detection device where each of the sound waves generated oscillate at a specific frequency, or number of vibrations or cycles per second, which utilize frequencies between 500,000 and 10,000,000 cycles per second (500 KHz to 10 MHz). At frequencies in the megahertz range, sound energy does not travel efficiently through air or other gasses, but it travels freely through most liquids and common engineering materials and solids; (iii) An acoustic velocity based device where the speed of a sound wave varies depending on the medium through which it is traveling, affected by the medium's density and elastic properties. Different types of sound waves will travel at different velocities; and (iv) An acoustic wavelength based device where any type of wave will have an associated wavelength, which is the distance between any two corresponding points in the wave cycle as it travels through a medium. Wavelength is related to frequency and velocity by the simple equation: $\lambda = c/f$ where: $\lambda$=wavelength; c=sound velocity; and f=frequency. Wavelength is a limiting factor that controls the amount of information that can be derived from the behavior of a wave. In the inventive acoustic frequency detection, the lower limit of detection for a discontinuity in target object 15 that can be recognized for effective flagging is one-half of the above-referenced wavelength because anything smaller than that will be invisible. In acoustic frequency detection thickness gauging, the theoretical minimum measurable thickness is one multiple of the above-referenced wavelength.

In terms one illustrative example of the novel method employed herein, and assuming the choice of an acoustic frequency detection based device, one essential step deserving of mention is that of comparative techniques. Using appropriate reference standards along with a knowledge of sound wave propagation and generally accepted acoustic test procedures, a trained operator identifies specific echo patterns corresponding to the echo response from target object portions without contraband, and from representative contraband that may be hidden therein. The echo pattern from a test piece may then be compared to the patterns from these calibration standards in order to determine its condition.

Straight beam testing may thereafter be employed as a step of preliminary testing, especially when the user intention is to avoid actually contacting the target object 15, by adjusting to the proper frequency for that application. More particularly, straight beam testing utilizing contact, delay line, dual element, or immersion transducers is generally employed to find discontinuities parallel to the surface of the test piece, as well as voids and porosity. It utilizes the basic principle that sound energy traveling through a medium will continue to propagate until it either disperses or reflects off a boundary with another material, such as the air surrounding a far wall or outside a target object 15. In this type of test, the operator couples transducer 25 to a test piece (not depicted) and locates the echo returning from the far wall of the test piece, and then looks for any echoes that arrive ahead of that back wall echo, discounting grain scatter noise if present. An acoustically significant echo that precedes the back wall echo implies the presence of a discontinuity (i.e., contraband) in target object 15. Through further analysis, the depth, size, and shape of the structure producing the reflection can be determined. Consequently, sound energy will travel to the far side of a part of a specimen, but reflect earlier if a discontinuity is presented. This dynamic is altered in the present invention by designing the unit to a very specific frequency and wavelength, so as to prevent this reflection from happening, in order to detect molecular structure (such as the illustrative Nitrogen) and therefore, so as to detect the elements that make up that given structure. Straight beam testing may be instituted as one part of the overall novel system herein to first ensure penetration of the container portion of target object 15. Once inside the container, the frequency and wavelength can be fined tuned to generate the desired distance for the wave to travel and consequently, for determining (once inside target object 15) the wavelength needed to ensure everything in the container is being captured and returned, but as alluded to above, this is predicated on ensuring proper penetration of the correct target object 15.

In some specialized cases, testing may be performed in a "through transmission mode", where sound energy travels between two transducers placed on opposite sides of the test piece. If a large discontinuity is present in the sound path, the beam will be obstructed and the sound pulse will not reach the receiver. The angled sound beam is highly sensitive to discontinuities perpendicular to the far surface of the test piece (first leg test) or, after bouncing off the far side, to discontinuities perpendicular to the coupling surface (second leg test). A variety of specific beam angles and probe positions are used to accommodate different part geometries and discontinuities types, and these are described in detail in appropriate inspection codes and procedures.

As referenced above with regards to FIG. 5, an electron counter may be employed in one embodiment of the invention. One example of this electron counter is a vacuum-tube structure that multiplies incident charges. In a process called secondary emission, a single electron can, when bombarded on secondary emissive material, induce emission of roughly 1 to 3 electrons. If an electric potential is applied between this metal plate and yet another, the emitted electrons will accelerate to the next metal plate and induce secondary emission of still more electrons. This can be repeated a number of times, resulting in a large shower of electrons all collected by a metal anode, all having been triggered by just one. This avalanche can be triggered by any charged particle hitting the starting electrode with sufficient energy to cause secondary emission, and consequently, the electron counter may be seen as being used as an ion detector this avalanche can also be triggered by a photon causing vacuum photoemission of at least one electron. In a photomultiplier tube, a photo-emissive surface is followed by an electron counter with several sequential multiplying electrodes called dynodes. Because these electrodes are separate from each other, this might be called a "discrete-dynode" multiplier. A voltage divider chain of resistors is usually used to place each dynode at a potential 100-200V more positive than the previous one. The end result of this is that the novel device can derive molecular structure for use in detecting "flagged" elements.

A "continuous-dynode" structure is feasible if the material of the electrodes has a high resistance so that the functions of secondary-emission and voltage-division are merged. A "continuous-dynode" structure is important to the present invention because of the need to count electrons. This is effectuated through building a funnel of glass coated inside with a thin film of semi-conducting material, with negative high voltage applied at the wider input end, and positive voltage near ground applied at the narrower output end. Electrons emitted at any point are accelerated a modest distance down the funnel before impacting the surface, perhaps on the opposite side of the funnel. At the destination end a separate electrode (anode) remains necessary to collect the multiplied electrons.

Alternatively, one embodiment contemplates employing a different geometry of continuous-dynode electron multipliers called a micro-channel plate. A micro-channel plate may be considered a 2-dimensional parallel array of very small continuous-dynode electron multipliers, built together and powered in parallel too. Each micro-channel is generally parallel-walled, not tapered or funnel-like. One might typically use the micro-channel plate variant in cases where ions are present.

Another important component within the overall inventive device is a data calculator which is used to separate the ions according to their mass-to-charge ratio. The data calculator relies in part on natural laws that govern the dynamics of charged particles in electric and magnetic fields in vacuum, where F is the force applied to the ion, m is the mass of the ion, a is the acceleration, Q is the ion charge, E is the electric field, and v×B is the vector cross product of the ion velocity and the magnetic field. Equaling the above expressions for the force applied to the ion yields effects in accordance with Maxwell's Laws of Electromagnetic Waves. This differential equation the motion for charged particles, such that the motion of the particle in space and time in terms of m/Q, or in other words, the illustrative signature of a flagged element of say, Nitrogen or the like could be thought of as being identified within the context of a "mass-to-charge spectrometer". When presenting data, it is common to use the (officially) dimensionless m/z, where z is the number of elementary charges (e) on the ion (z=Q/e). This quantity, although it is informally called the mass-to-charge ratio, more accurately speaking represents the ratio of the mass number and the charge number, z. By way of further example, it is noted that above signature includes other quantifiable dimensions, such as, in the case of, Nitrogen, the mass spectrometry signature has m/z peaks at 13 and 28, where the peaks are defined as the relative abundance of whatever element that is native to the target contraband (such as the illustrative Nitrogen found in most explosives) and that, consequently, is being detected. When graphed, the peaks result from relative abundance on the y axis and the m/z ratio on the x axis. Accordingly, a reading can be taken and then compared to this graph of the mass spectrometry signature of Nitrogen. Utilization of these peaks therefore offers signatures with multi-dimensional data fidelity.

There are several important data counter characteristics. The mass resolving power is the measure of the ability to distinguish two peaks of slightly different m/z. The mass accuracy is the ratio of the m/z measurement error to the true m/z. Mass accuracy is usually measured in parts per million (ppm) or milli-mass units (mmu). The mass range is the range of m/z amenable to analysis by a given mass analyzer. The linear dynamic range is the range over which ion signal is linear with analyte concentration. Speed refers to the time frame of the experiment and ultimately is used to determine the number of spectra per unit time that can be generated.

A sector field data calculator uses an electric and/or magnetic field to affect the path and/or velocity of the charged particles in some way. Sectors bend the trajectories of the ions as they pass through the data calculator, according to their mass-to-charge ratios, deflecting the more charged and faster-moving, lighter ions more, as seen in FIG. 7. The counter can be used to select a narrow range of m/z or to scan through a range of m/z to catalog the ions present.

Ion traps use the same physical principles as a quadrupole data counter, but the ions are trapped and sequentially ejected. Either may be employed within various embodiments of the present invention. Ions are trapped in a mainly quadrupole radio frequency (RF) field, in a space defined by a ring electrode (usually connected to the main RF potential) between two end cap electrodes (typically connected to DC or auxiliary AC potentials). The sample is ionized either internally (e.g. with an electron or laser beam), or externally, in which case the ions are often introduced through an aperture in an end cap electrode.

There are many mass/charge separation and isolation methods but the most commonly used is the mass instability mode in which the RF potential is ramped so that the orbit of ions with a mass a>b are stable while ions with mass b become unstable and are ejected on the z-axis onto a detector. There are also non-destructive analysis methods.

Ions may also be ejected by the resonance excitation method, whereby a supplemental oscillatory excitation voltage is applied to the end cap electrodes, and the trapping voltage amplitude and/or excitation voltage frequency is varied to bring ions into a resonance condition in order of their mass/charge ratio (output 73 in FIG. 7).

Wand 21 component includes acoustic wave detector 20 for the additional purpose of recording either the charge induced or the current produced when an ion passes by or hits a surface. In a scanning instrument, the signal produced in the detector during the course of the scan versus where the instrument is in the scan (at what m/Q) will produce a mass spectrum signature, a record of ions as a function of m/Q.

Figure 2B:
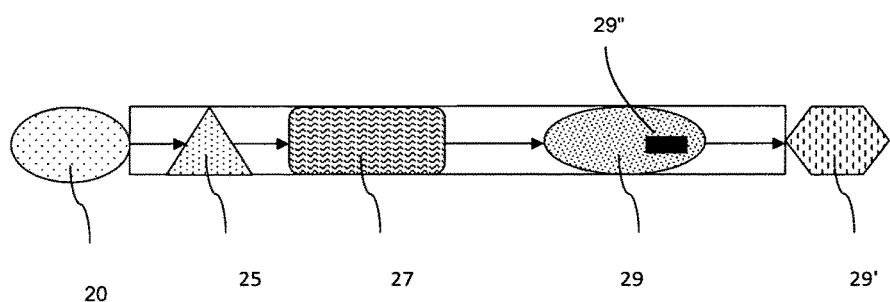

With electron counter 27 built into acoustic wave detector 20, this construction as depicted in FIG. 2B provides shielding for low level circuits and virtually eliminates ground loops. This also eliminates stray electromagnetic fields from the acoustic frequency detection generator. Electron counter 27 amplifies the signal currents to approximately 100000 times greater than the threshold values before they are introduced into the appropriate amplifiers/multipliers. The secondary emission electrons 57 in FIG. 5 will produce, by scanning, beams that are attracted toward a positively charged electrode in the electron multiplier 50 itself for structure. Electron multiplier 50 then serves as a wideband amplifier with good noise characteristics. Its output constitutes a resolvable detail of the electron acoustic image and once fed into the data calculator and the calculations of m/z ratio are made for each element being detected, will output the data we need to detect nitrogen by having an interface between the large transducer and the standard of Nitrogen (so that transducer 25 can communicate with standard 29) so that the signal and data retrieved conversion can be done so as to make a comparison between what is being detected and the standard. In one illustrative embodiment, a light or other alarm will go off once there is a match that indicates a positive reading, in accordance with the aforementioned. As discussed above, a corroborative method of detection in particular pure Nitrogen which is contained in explosives using what is called the "ratio output". It should be noted that this ratio output distinguishes between say, pure Nitrogen and say, Nitrogen 15 or Nitrogen ions, as the latter two are inert and generally not identified with explosives, and as such the inventive systems can differentiate the same within a given elemental class like "Nitrogen" and further eliminate false positives. In doing so, the inventive system 10 is configured to recognize that the illustrative pure Nitrogen has a very specific ratio output signal which looks like one half of a parabola. This half-parabola output signal is furthermore, unique to pure Nitrogen, and similarly, other elements have their own unique signatures that identify them respectively. This can be detected from acoustic frequency detector 20 directly and will be compared to the mass spectrometry signature being detected. If these values are the same then an alarm will be triggered. The ratio output signal will ensure that the error rate false positives) is nearly zero.

Crystalline Material Preparation for Oil Suspension Embodiment and Crystalline Structure Embodiment Various types of ceramic crystals may be employed within the present invention. However, for maximizing both the propagation and return of the output signal from the resultant crystalline based transducer, in one embodiment, a ferroelectric ceramic compound having the composition of the following formula of: $s[L]-x[P]y[M]z[N]p[T]$. The illustrative ferroelectric ceramic crystals according to the present invention are relax or ferroelectrics having high piezoelectricity, a high electromechanical coefficient and a high electro-optical coefficient, and are particularly amenable to maximizing the performance of the novel acoustic wave device, especially when the system is not actually physically contacting the target object. The process of preparing the single crystal according to the present invention enables preparation of crystals having a diameter of various proportions, starting at approximately less than 1 mm or less, with uniform composition across the dispersal. In the above formula, [P] is lead oxide, [M] is magnesium oxide or zinc oxide, [N] is niobium oxide, [T] is titanium oxide, [L] is one selected from the group consisting of lithium tantalate or lithium niobate, lithium, lithium oxide, platinum, indium, palladium, rhodium, nickel, cobalt, iron, strontium, scandium, ruthenium, copper, yttrium, and ytterbium or mixtures thereof, and x, y, z, p and s are defined as $0.55<x<0.60$, $0.09<y<0.20$, $0.09<z<0.20$, $0.01<p<0.27$ and $0.01<s<0.1$, respectively. The size of such particles is illustratively described as being between diameter 1 and 10 µm, especially 1 and 5 µm, particularly 1 and 3 µm, when prepared with an exemplary method such as ultrasonic radiation.

Piezo-ceramic materials are categorized as functional ceramics, and when placed in the transmit/receive array of wand 21 as sensors, the aforementioned unique ceramic composition makes it possible to convert forces, pressures and accelerations into electrical signals. In the case of sonic and ultrasonic transducers and actuators, the ceramic composition converts electric voltages into vibrations or deformations and/or sound waves into electromagnetic wave, and has great variability in adjusting to any desired frequency. It is this wave that will carry information needed to analyze further once the conversion via the transducer is done. Depending on the specific field of use of the present application (e.g., whether target objects such as scanning luggage versus automobiles, and whether flagging materials such as Nitrogen based explosives versus carbon based smuggled gems), the piezo-ceramic materials may differ. To this end, it is noted that piezo-ceramic materials, while generally classified according to their chemical composition, the specific application conditions may similarly govern their specific selection for use in wand tip 21. The particular piezo-ceramic may also be chosen in one embodiment because of its crystal size, and the optimal size may be is determined by matching the crystal size with the flagged element of targeted contraband within a target object. For example, most explosives are Nitrogen based, and when flagging Nitrogen, the molecular size of Nitrogen is such that it best responds to frequencies in the range of approximately 28.905 MHz for solid/liquid forms, and approximately 9.81 MHz for gaseous forms. Given this, piezo-ceramics such as PZT ceramics are ideal because their crystal size is generally very small, and this feature provides much more surface area and as a result, a very stable focused beam and furthermore, also helps to stabilize the acoustic wave being transmitted, as well as making it easier to control this dynamic therefore produces an optimized return reflection to wand tip 21 by setting the strength of the detector by fine tuning so that once the beam penetrates target object 15 (i.e. a bag, luggage, container, or a person) the user can adjust and control the same so as to spread out once it penetrates the inside of target object 15, into a size however large or small as may be desired. Consequently, the user can control both how far the beam (acoustic wave) travels, and where it rebounds back. This function involves a feature called a cyclical waveform, an aspect that also carries the frequency along with it during transmission. As previously discussed because frequency and waveform are inverse operations from one another, if the velocity of the sound wave is known, the frequency can be calculated once the waveform returns, or vice a versa. This dynamic may be illustratively applied in the case of say, scanning for smuggled gems. In such a case, one might optimize the present invention by flagging Carbon, instead of Nitrogen. This field of application might be customized by utilizing crystals such as Quartz because this mineral has a surface area that maximizes the proper output and input from in relation to the target element, which in this case, has a size of less than 0.1 Micrometers.

Further to the above, aggregate crystal surface area is a key factor in optimization. The smaller the crystals, the greater the surface area realized, and this is an important factor in creating an optimal contraction of crystals in order to achieve a very wide range of acoustic frequencies and wavelengths that will encompass the entire area being detected and analyzed. Subsequently, the proper frequency and wavelength to penetrate target object 15, such as luggage, can now be adjusted so that the proper area therein is being completely analyzed. Some additional, illustrative parameters that may factor on the selection of the particular on piezo-ceramic properties are as listed as follows:

| Selection of Piezo-ceramic Properties | | | |
|---|---|---|---|
| | Power transducers | Sensors | Actuators |
| Relative permittivity $\varepsilon_{33}{}^{\tau}/\varepsilon_0$ | 1,000-1,300 | 1,500-1,850 | 1,800-3,800 |
| Loss factor tan δ | $2 \times 10^{-3}$- $3 \times 10^{-3}$ | $12 \times 10^{-3}$- $20 \times 10^{-3}$ | $15 \times 10^{-3}$- $16 \times 10^{-3}$ |
| Frequency constant $N_P$, KHz · mm | 2,210-2,280 | 2.020-2,050 | 1,960-2,010 |

-continued

| Selection of Piezo-ceramic Properties | | | |
|---|---|---|---|
| | Power transducers | Sensors | Actuators |
| Coupling factor $k_P$ | 0.55-0.57 | 0.59-0.62 | 0.65 |
| Charge constant $d_{33}$, $10^{-12}$ C/N | 240-310 | 390-450 | 475-680 |
| Voltage constant $g_{33}$, $10^{-3}$ Vm/N | 26.9-27.1 | 26.9-33.1 | 20.2-28.5 |
| Elastic compliance $S_{11}{}^{\varepsilon}$, $10^{-12}$ m²/N | 11.4-14.9 | 16.3-18.5 | 15.8-17.9 |
| Elastic stiffness $C_{33}{}^{D}$, $10^{10}$ N/m² | 15.9-16.2 | 14.5-15.8 | 14.7-15.2 |
| Density g/cm² | 7.65-7.70 | 7.65-7.80 | 7.70-7.83 |
| Quality $Q_m$ | 500-1,000 | 60-90 | 75-80 |
| Aging rate $C_\varepsilon$, % | -4.5 to -3.0 | -2.3 to -0.3 | -1.6 to -0.8 |

Once prepared, the particulate matter may be formed a s a crystalline surface structure embodiment, as discussed below, or as a crystalline oil suspension embodiment wherein the prepared crystals are prepared as particulates to be suspended by use of a mixing means, with oil to prepare the crystalline oil suspension. Various amounts of crystal particulates (piezoelectric ceramic) maybe mixed into the oil, with the understanding that in one embodiment, greater relative amounts of crystalline particulates to oil may be preferred in order to maximize the "push" (squeeze) effect of the damper(s) 64 element(s) on the suspended crystals as described herein. Specifically, with an illustrative amount of say, 2 gm of particulate matter mixed with say, 25 mL of oil will result in >10%, and more preferentially, between 40-85% reduction in interstitial space between the suspended particulate matter (crystals) when voltage is applied. This measure of damping effect (termed herein as a novel "interstitial reduction") helps mitigate unwanted effects resulting from attenuation. Essentially, the attenuation effects incumbent upon the acoustic waves interacting with the crystals in between damping elements, such that when voltage is applied, the damping element(s) will squeeze the crystals such that any interstitial spaces will be minimized. Many different oils may be employed, but illustratively one type of oil that maybe employed is crude oil light, having a viscosity between 10 cp and 100 cp. Most preferably the mixing means should be non-grinding e.g. a non-grinding magnetic stirrer or an overhead stirrer (particularly a non-grinding magnetic stirrer). Desirably, stirring speed will be set at a level that gives efficient mixing in the mixing chamber, but without inducing vortex effects. Vortex effects are undesirable since they may cause particle size reduction through liquid micronization-like processes.

After the crystalline oil suspension has been prepared, it (or at least just the oil, as described in the alternative embodiment above) must be encapsulated in a polymer casing, thereby forming the encapsulation that comprises the tip of wand 21 seen in FIG. 2A. Whether provided as a piezoelectric ceramic layer in the "crystalline surface structure embodiment" as described below, or as a piezoelectric ceramic mixed within as in the "encapsulated oil suspension embodiment" of the crystalline oil suspension, the encapsulation and any crystalline preparation is appurtenant (physically and/or electronically in connection with transducer 25). In one alternative embodiment, the crystalline oil encapsulation maybe made as a "swappable medium module" that may be easily replaced (swapped) out from the tip of wand 21 by a user, where the user desires to replace worn out or broken crystalline oil encapsulation, or in one illustrative embodiment, desires to swap out one crystalline oil encapsulation with another crystalline oil encapsulation based upon the particular characteristics of the given piezoceramics in the crystalline oil encapsulation. By way of example, where inventive device 20 is being used to detect or flag Nitrogen (for explosives detection) and then the user needs to employ inventive device 20 for say, gem smuggling detection (Carbon flagging), then the swappable medium module feature may be employed, whereby the crystalline oil encapsulation having crystals such as ceramic (e.g., piezo-ceramic materials that have been specifically optimized for Nitrogen flagging) in the oil suspension may be swapped out for the crystalline oil encapsulation having crystals such as Quartz (e.g., piezo-ceramic materials that have been specifically optimized for Carbon flagging). In either case, by way of just one illustrative embodiment the fabrication of pertaining to tip of wand 20, oil such as any standard commercial oil having a viscosity between 10 and 100 centipose as a medium, and with the aforementioned piezo-ceramic crystals suspended therein, the resulting suspension may be encapsulated on top of a mesh interface to create a specific piezoelectric effect that will differ from ordinary, known piezo results. Note that the piezo-ceramics in the crystalline oil encapsulation are, in one embodiment, used for three specific functions, namely: (i) transducer medium; (ii) actuator medium (e.g., propagating or transmitting the acoustic waves to target object 20); and (iii) sensor array medium (e.g., receiving reflected or returned the acoustic waves from target object 20).

Alternatively, the above effects may also be achieved in one variant of the present invention through the use of the preparation pertaining to the crystals and oil of the aforementioned "encapsulated oil suspension embodiment", but without the crystalline material being suspended therein. In such an alternative embodiment (hereby termed the "crystalline surface structure embodiment" or "unadulterated oil encapsulation embodiment"), the crystalline production as described above may instead be formed as a substantially continuous, formed layer at tip 68 of wand 20 which forms a crystalline surface structure that is adjacent to a separate oil encapsulation that is similar to the previously described oil suspension encapsulation, but is an unadulterated oil encapsulation that contains zero or almost zero particulate materials suspended therein. This layer (not depicted) may be of various diameters of width and thickness, depending on the field of application. In the above-described field, one illustrative embodiment might have approximately 1.5 inches of thickness and a diameter of such dimensions that it reflects the multiple of wavelengths being propagated and/or captured. Either way, this layer also has damper 64 adjacent (typically abutting one end of the layer, opposite the side of the layer where the unadulterated oil encapsulation abuts the layer) so that the "interstitial reduction" as described above. Provision of this permits the beneficial acoustic wave processing properties of the crystalline materials acting in concert with the oil, whereby the propagation and reception of such waves are magnified in such a way so as to afford the superior detection of discontinuities such as Nitrogen or the like in target object 15.

A signal will be returned from the item being screened and sent to an electron counter, which will calculate the charge of the electrons and the number of electrons per element, then those calculations will be fed into a data calculator to calculate the m over z ratio (the mass over charge ratio) and the value of the matter detected (i.e., density, mass, and molecular structure). The ratio and matter results will be sent to an interface which will compare those values to the standard signature of the element being sought. For example if the "flagged" element is nitrogen, the results will be compared to the known nitrogen m/z ratio peaks occurring at 13 and 28. If there is a match between the detected results and the standard an alarm on the end of wand will be triggered. In one alternative embodiment, a portable printer or readout may be connected or otherwise situated with the wand to print a receipt or read out with the density and mass details detected.

In terms of fields of use, the novel system and method will be particularly useful in airports to send a signal right through a luggage bag or on a person to detect for nitrogen. However, other fields of use might include: (i) military; (ii) police; (iii) security used at stadiums or a large events, large office buildings, theaters, etc., where the novel device can protect citizens from explosive devices or other threats. It is noted that the above fields of use may entail both stationary and mobile variants of the present invention. To this end, a mobile variant (or even the stationary variant) may utilize convenient structural features such as adjustable swing arms, user operated detachable wands where wand 21 is detachable from acoustic wave detector 20 and internally powered or otherwise rechargeable and fully in communication with acoustic wave detector 20 via wireless communication modules.

While the methods contained herein constitute preferred embodiments of the invention, it is to be understood that the invention is not limited to these precise methods, and that changes may be made therein without departing from the scope of the invention which is defined in the appended claims.

What is claimed is:

1. A method of non-destructively identifying contraband materials, said method comprising:
    transmitting an output wave from a crystalline based transducer, said transducer being operatively positioned as an acoustic detector which collects a return acoustic wave;
    collecting said return acoustic wave having an acquired resonant frequency of at least one at least one atom of a target, at an array coupled via a connector to said crystalline based transducer;
the method further comprising the steps of:
    counting electrons associated with materials in said target object via a connection with said crystalline based transducer;
    analyzing, through a signal processing assembly, frequency changes by comparing said output acoustic wave with said return acoustic wave;
    outputting a comparator value for at least one material in said target object, said value being derived from values obtained from said counting electrons and analyzing steps;
    comparing said comparator value with at least one established baseline value for contraband materials; and
    outputting a notification when said comparator value is equivalent to said baseline value for contraband materials.

2. The method of claim 1, further comprising usage of signatures with multi-dimensional data fidelity.

3. The method of claim 2, further comprising bifurcated double verification during flagging of suspicious materials.

4. The method of claim 3, wherein said step of transmitting an output wave from a crystalline based transducer to a target without physical contact comprises transmission said output wave through a piezoelectric ceramic material oil suspension encapsulation connected with said transducer.

5. The method of claim 3, wherein said step of transmitting an output wave from a crystalline based transducer comprises transmission said output wave through a piezoelectric ceramic surface structure and through an unadulterated oil encapsulation.

6. The method of claim 4 or 5, wherein said step of comparing said comparator value with at least one established baseline value for contraband materials includes comparing a resonant frequency signature and a mass spectrometry signature.

7. The method of claim 6, further comprising the step of at least one of the following of: (i) preliminary testing straight beam testing; or (ii) through transmission mode.

8. The method of claim 7, wherein said step of transmission through a piezoelectric ceramic includes the use of lead zirconate titanate $(Pb[Zr(x)Ti(1-x)]O_3)$ (PZT).

9. An apparatus for non-destructively identifying contraband materials, said apparatus comprising:
- a crystalline based transducer with an acoustic detector for propagating an output acoustic wave and collecting a return acoustic wave, said return acoustic wave acquiring a resonant frequency from at least one atom of a target object;
- an electron counter coupled via a connector to said crystalline based transducer for counting electrons associated with materials in said target object;
- a signal processing assembly for analyzing frequency changes by comparing said output acoustic wave with said return;
- a data calculator for:
  (i) outputting a comparator value for at least one material in said target object, said value being derived from values obtained from said counting electrons and analyzing steps;
  (ii) comparing said comparator value with at least one established baseline value for contraband materials; and
  (iii) outputting a notification when said comparator value is equivalent to said baseline value for contraband materials.

10. The apparatus of claim 9, wherein said data calculator is configured to employ signatures for outputting multi-dimensional data fidelity.

11. The apparatus of claim 10, wherein said data calculator is configured to employ bifurcated double verification during flagging of suspicious materials.

12. The apparatus of claim 11, wherein said crystalline based transducer includes a piezoelectric ceramic material oil suspension appurtenant to said transducer.

13. The apparatus of claim 11, wherein said crystalline based transducer includes a piezoelectric ceramic surface structure and an unadulterated oil encapsulation.

14. The apparatus of claim 11 or 12, wherein data calculator is configured to compare said comparator value with at least one established baseline value for contraband materials includes comparing a resonant frequency signature and a mass spectrometry signature.

15. The apparatus of claim 14, wherein said acoustic wave device is configured to generate acoustic waves through at least one of the following of: (i) preliminary straight beam testing; or (ii) through transmission testing.

16. The apparatus of claim 15, wherein said piezoelectric ceramic material oil suspension includes lead zirconate titanate $(Pb[Zr(x)Ti(1-x)]O_3)$ (PZT).

17. The apparatus of claim 15, wherein said encapsulation is a swappable medium module.

* * * * *